United States Patent [19]

Jones

[11] Patent Number: 5,386,822
[45] Date of Patent: Feb. 7, 1995

[54] RESUSCITATION APPARATUS

[76] Inventor: Martin E. Jones, 3117 Nelson Ave., North Las Vegas, Nev. 89030

[21] Appl. No.: 751,749

[22] Filed: Aug. 29, 1991

[51] Int. Cl.⁶ .............................................. A61M 16/00
[52] U.S. Cl. ............................ 128/203.11; 128/202.28
[58] Field of Search ...................... 128/202.28, 202.29, 128/203.11

[56] References Cited

U.S. PATENT DOCUMENTS

| | | | |
|---|---|---|---|
| 4,834,085 | 5/1989 | Webster, II | 128/203.11 |
| 4,856,506 | 8/1989 | Jinotti | 128/203.11 |
| 4,942,873 | 7/1990 | Irwin et al. | 128/203.11 |
| 4,944,291 | 7/1990 | Robertson, II et al. | 128/203.11 |
| 4,998,530 | 3/1991 | DonMichael | 128/203.11 |
| 5,005,568 | 4/1991 | Loescher et al. | 128/203.11 |

Primary Examiner—Edgar S. Burr
Assistant Examiner—Aaron J. Lewis

[57] ABSTRACT

Simple compact apparatus for artificial resuscitation which avoids mouth-to-mouth contact. The apparatus enables a person to force exhaled air from his lungs into the lungs of a victim without mouth-to-mouth contact, the air flow being controlled by a flutter valve, so that air flows only from the person to the patient, with any fluid exhaled by the patient being by-passed around the valve and through appropriate outlets to the atmosphere.

1 Claim, 2 Drawing Sheets

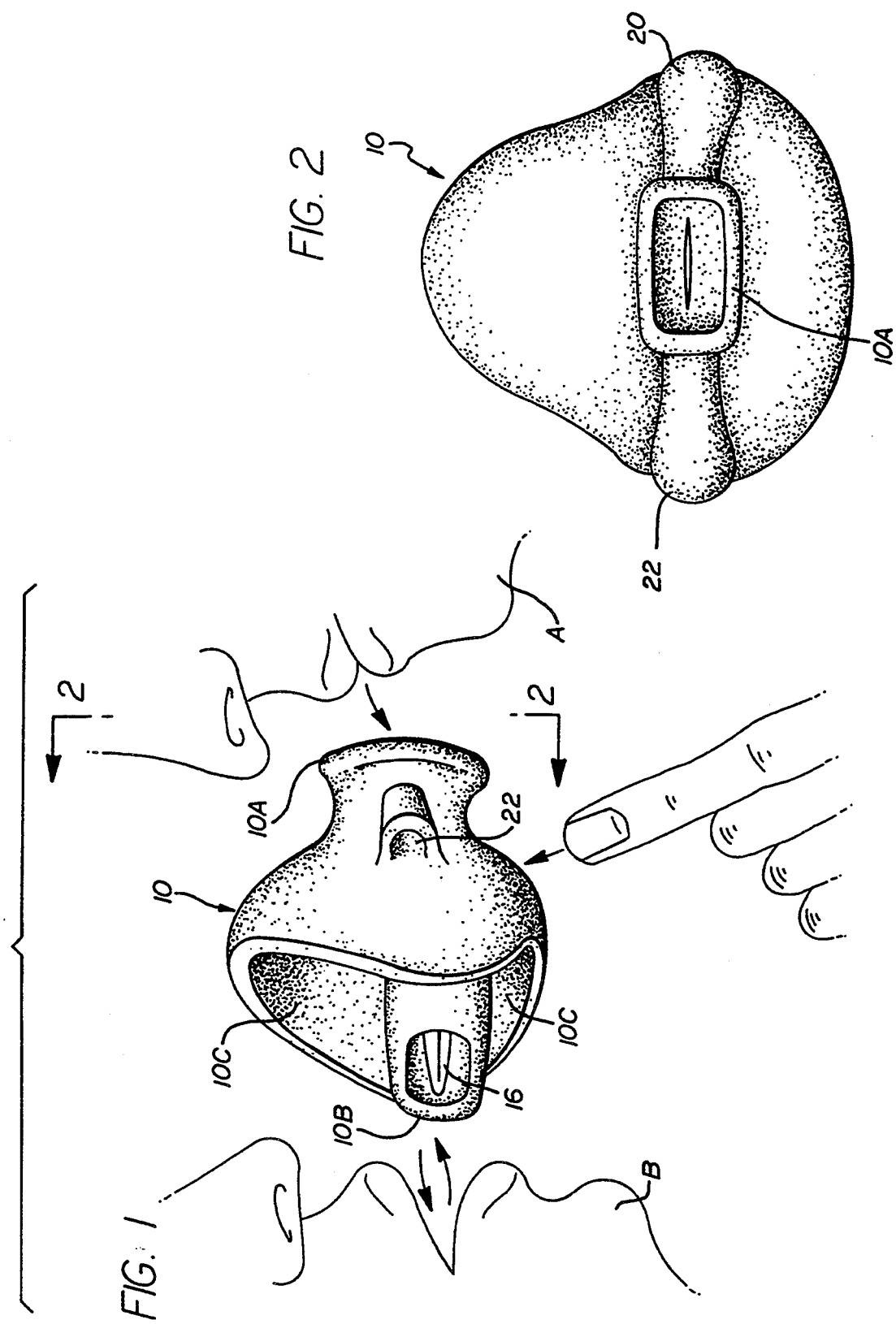

RESUSCITATION APPARATUS

RELATED CASE

Ser. No. 819,684, filed Jan. 17, 1986, in the name of the present inventor, entitled "Resuscitation Apparatus" (Now Abandoned).

BACKGROUND OF THE INVENTION

A well known successful method for reactivating normal breathing in a person who has stopped breathing due to drowning, electrical shock, or various other reasons, is by mouth-to-mouth resuscitation, by which another person exhales air directly from his lungs at rhythmic intervals into the lungs of the victim placing his mouth in contact with the mount of the victim.

Such mouth-to-mouth resuscitation is currently widely practiced. However, a drawback to mouth-to-mouth resuscitation is the natural abhorrence by anyone to place his mouth against the mouth of another person, especially a stranger, an also the fear of contracting a disease from such a contact.

For that reason, a variety of devices have been proposed in the prior art for effectuating mouth-to-mouth resuscitation without actual contact with the mouth of the victim. However, for the most part such prior art devices have been unduly complex and awkward to use.

It is accordingly an objective of the present invention to provide a simple and compact apparatus which may be disposable, or which may be readily sterilized, and which may be used for effectuating mouth-to-mouth resuscitation without any actual mouth contact with the patient.

BRIEF DESCRIPTION OF THE DRAWINGS

FIG. 1 is a perspective representation of one embodiment of the apparatus of the invention and a schematic representation of the manner in which the apparatus may be used;

FIG. 2 is an end view of the apparatus of FIG. 1 taken essentially along the line 2—2 of FIG. 1.

DETAILED DESCRIPTION OF THE ILLUSTRATED EMBODIMENT

Figure 3:
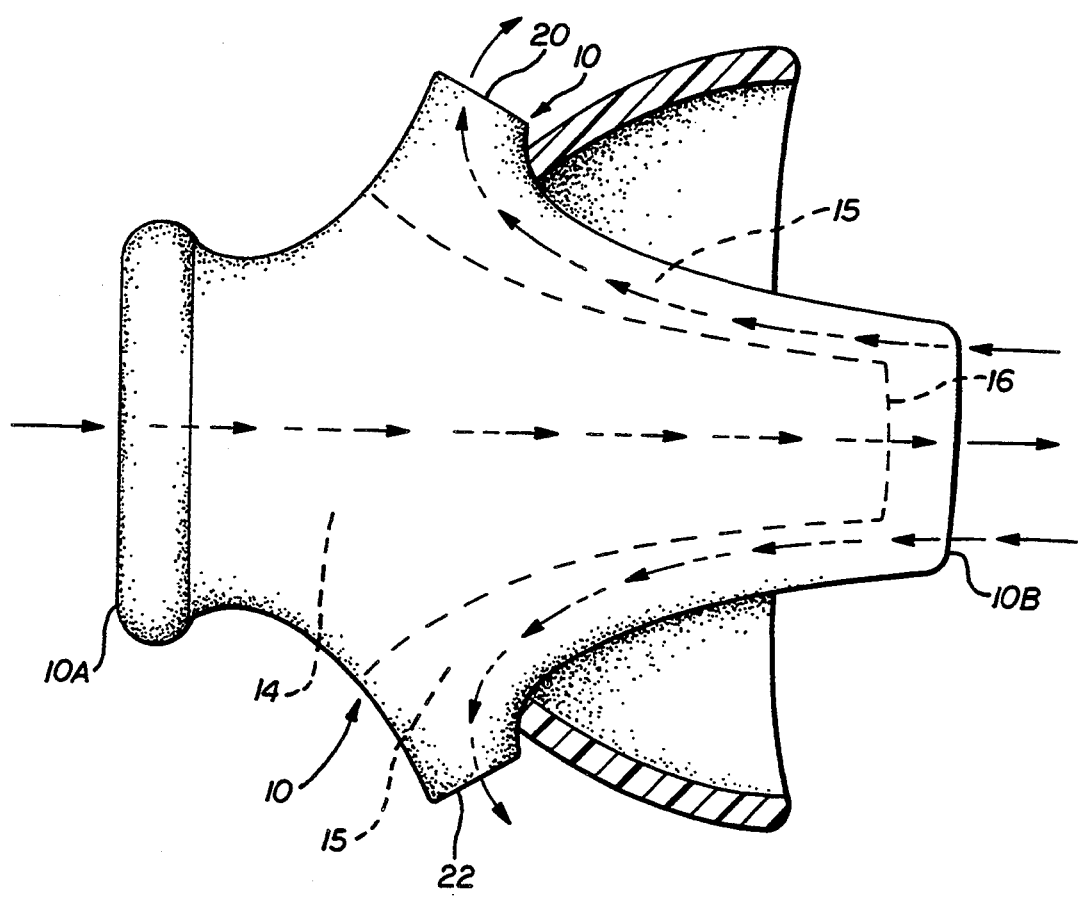
FIG. 3 is a sectional schematic representation of the apparatus showing the manner in which it operates.

The apparatus shown in FIGS. 1, 2 and 3 comprises a molded housing 10 which may be formed of any appropriate pliable plastic material, such as polyethylene, polyurethane or polypropylene.

The housing 10 defines a first mouthpiece 10A at one end which is intended to be inserted into the mouth of a person A administering the resuscitation. The housing also defines a second mouthpiece 10B at the other end which intended to be inserted into the mouth of a patient or victim B receiving the resuscitation. The housing also forms a cup-shaped mask 10C which is shaped and positioned to fit around the mouth of the patient or victim B.

As best shown in FIG. 3, housing 10 defines a first passage 14 between mouthpiece 10A and mouthpiece 10B, and a flutter valve 16 is positioned in the first passage, so that air may flow only from the mouthpiece 10A to the mouthpiece 10B. The housing 10 also forms a second passage 15 between mouthpiece 10B and a pair of outlets 20, 22 on opposite sides of the housing. Any fluid exhaled by the patient or victim into the mouthpiece 10B flows through the second passage 15 to the outlets 20 and 22.

In operation, the person A administering the resuscitation breathes into the mouthpiece 10A and forces his exhaled air in the direction of the arrows in FIG. 3 through passageway 14 and through flutter valve 16 to mouthpiece 10B, and from there into the lungs of the patient or victim B.

The administering person A breathes into the mouthpiece 10A on a rhythmic periodic basis, and while he does so, he covers the outlets 20 and 22 with the fingers of one hand. In the intervals between the exhaling by the administering person, he removes his fingers from the outlets 20 and 22, so that any fluid exhaled by the victim or patient flows in the direction of the arrows in the FIG. 3 through the passage 15, and through outlets 20 and 22 to the atmosphere.

The invention provides, therefore, an improved, inexpensive and compact apparatus which is easy to operate, and which provides an efficient means for administering mouth-to-mouth resuscitation.

It will be appreciated that while a particular embodiment of the invention has been shown and described, modifications may be made, and it is intended in the following claims to cover all modifications which come within the true spirit and scope of the invention.

I claim:

1. Resuscitation apparatus including a one-piece housing having a first end and a second end and defining a first mouth piece at said first end to be inserted into the mouth of a person administering the resuscitation and defining a second mouth piece at said second end to be inserted into the mouth of a person receiving the resuscitation, said housing also forming a cup-shaped mask at said second end surrounding said second mouthpiece configured and positioned to encompass the mouth of the receiving person, and said housing forming a central portion defining a first passage between the first and second mouth pieces; and said housing further defining a flutter valve means extending across said first passage for permitting air to flow through said first passage in one direction only from the first mouthpiece to the second mouthpiece; said housing having at least one outlet therein, and said housing defining a second passage around the periphery of said central portion to provide a communication between said second mouthpiece and said outlet to permit fluid flow from said second mouthpiece to said outlet.

* * * * *